United States Patent [19]

Bailey

[11] Patent Number: 5,642,995
[45] Date of Patent: Jul. 1, 1997

[54] DENTAL PROPHYLAXIS ANGLE WITH SEAL PROTECTOR

[75] Inventor: Ronald L. Bailey, Harvester, Mo.

[73] Assignee: Young Dental Manufacturing Company, Earth City, Mo.

[21] Appl. No.: 515,826

[22] Filed: Aug. 16, 1995

[51] Int. Cl.⁶ .................. A61C 1/05; A61C 1/16; A61C 3/06
[52] U.S. Cl. .................. 433/115; 433/116; 433/125
[58] Field of Search .................. 433/116, 125, 433/166, 115

[56] References Cited

U.S. PATENT DOCUMENTS

| | | | |
|---|---|---|---|
| 1,216,311 | 2/1917 | Hartman | 433/125 X |
| 1,837,938 | 12/1931 | Young | 433/166 |
| 2,451,918 | 10/1948 | Chott | 433/166 |
| 2,707,329 | 5/1955 | Costoff | 433/166 |
| 2,943,343 | 7/1960 | Jankelson | 433/166 X |
| 3,407,502 | 10/1968 | Richmond | |
| 3,436,830 | 4/1969 | Richmond | |
| 3,478,433 | 11/1969 | Richmond | |
| 3,786,566 | 1/1974 | Jalicic et al. | 433/116 |
| 3,789,462 | 2/1974 | Reich | |
| 4,253,832 | 3/1981 | Bailey | 433/115 |
| 4,292,027 | 9/1981 | Richmond | 433/127 |
| 4,365,956 | 12/1982 | Bailey | 433/115 |
| 5,040,978 | 8/1991 | Falcon et al. | 433/125 |
| 5,178,538 | 1/1993 | Eckert | 433/125 |

*Primary Examiner*—Nicholas D. Lucchesi
*Attorney, Agent, or Firm*—Polster, Lieder, Woodruff & Lucchesi

[57] ABSTRACT

A dental prophylaxis angle includes a body defining a sleeve and a head. A drive assembly is rotatably mounted in the sleeve. A driven gear is rotatably received in the head to be driven by the drive assembly. A cap is mounted in the head to close the head and retain the driven gear in place in the head. A threaded bur tube on the driven gear extends into a stem portion of the cap. The stem portion includes an externally beveled annular knife edge which forms a seal with a dental tool, such as a prophy cup, which is threaded into the bur tube. A protector ring on the cap surrounds the knife edge to prevent damage to the knife edge should the angle be dropped or otherwise contact a hard surface. The protector ring is spaced from the stem sufficiently to permit an elastomeric portion of the dental tool to extend between the stem and the ring.

22 Claims, 3 Drawing Sheets

DENTAL PROPHYLAXIS ANGLE WITH SEAL PROTECTOR

BACKGROUND OF THE INVENTION

This invention relates to dental prophylaxis angles, and in particular to a dental prophylaxis angle which provides a long-lasting positive seal with a dental tool.

Dental prophylaxis angles (prophy angles) include a body part which carries a drive gear for attachment to a Doriot type handpiece and a head which carries a driven gear in engagement with the drive gear. A dental tool such as a prophy cup is carded by the driven gear. In one popular style of prophy angle, the driven gear includes an internally threaded bur tube, and the dental tool includes a threaded shank which screws into the bur tube. The bur tube extends into a cap which closes the head of the angle.

Some present angles, such as the angle sold under the name TS2 by Young Dental of Earth City, Mo., create a seal between the cap of the metal angle and the prophy cup which is secured to the angle. The TS2 angle provides a knife edge in the cap which cuts into a bottom edge of the cup to create a seal with the cup. One particularly effective manner of forming the seal with a specially designed dental tool is described my U.S. Pat. No. 5,484,284, which is incorporated herein by reference. A prophy cup in accordance with that application has been on sale for more than a year.

The knife edge on the cap of the TS2 angle is sufficiently delicate that it can be bent or chipped if the angle is accidentally dropped or bumped against a hard, sharp surface. When the knife edge is bent or chipped, the angle cap may not form a tight seal with the prophy cup. Debris, such as grit, saliva, etc., therefore may find its way into the inner workings of the angle. This can shorten the useable life of the angle.

SUMMARY OF THE INVENTION

One object of the present invention is to provide a dental prophy angle which provides a particularly good seal between the angle and a dental tool attached to it.

Another object of the present invention is to provide such an angle which includes a means for protecting its sealing elements which seal with the prophy cup.

These and other objects will become apparent to those skilled in the art in light of the following disclosure and accompanying drawings.

In accordance with the present invention, generally stated, an improved dental prophylaxis angle is provided having a hollow stem through which a rotatable bur tube extends, the hollow stem having a sharpened edge which extends axially above an axial end of the bur tube, and a protector wall which surrounds and protects the sharpened edge. The protector wall is slightly taller than the hollow stem to protect the knife edge from damage should the angle be dropped or bumped against a hard surface.

As disclosed in my U.S. Pat. No. 5,484,284, an effective way to form a seal with the stem on the prophylaxis angle is with a dental tool having an elastomeric bottom surface formed as a ring around a metal screw part.

In accordance with the present invention, the elastomeric ring and the protective wall are sized to allow the outer part of the elastomeric ring to fit within the protector wall and, preferably, to leave a slight gap between an outer surface of the elastomeric ring and the inner surface of the protector wall when the dental tool is tightened onto the bur tube and the annular knife edge of the stem cuts into the elastomeric surface. Alternatively, the elastomeric ring on the dental tool is sized to touch the inside surface of the protector wall.

The protector wall is preferably several times the thickness of the knife edge of the stem. Typically, the knife edge has a thickness of about 0.005" and the protector wall has a thickness of about 0.020". The protector wall is preferably spaced about 0.020" to about 0.040" from the knife edge.

The protector wall is preferably continuous, but gaps, scallops, or crenelations may be provided if desired.

Prior to the invention of the prophy cup disclosed in my U.S. Pat. No. 5,484,284, the protector wall of the present invention would have rendered the TS2 angle inoperative. The cup of that application, however, has made possible an angle which retains its ability to seal better, and is far more resistant to abuse than, previously known prophy angles.

DESCRIPTION OF THE PREFERRED EMBODIMENT

Figure 1:
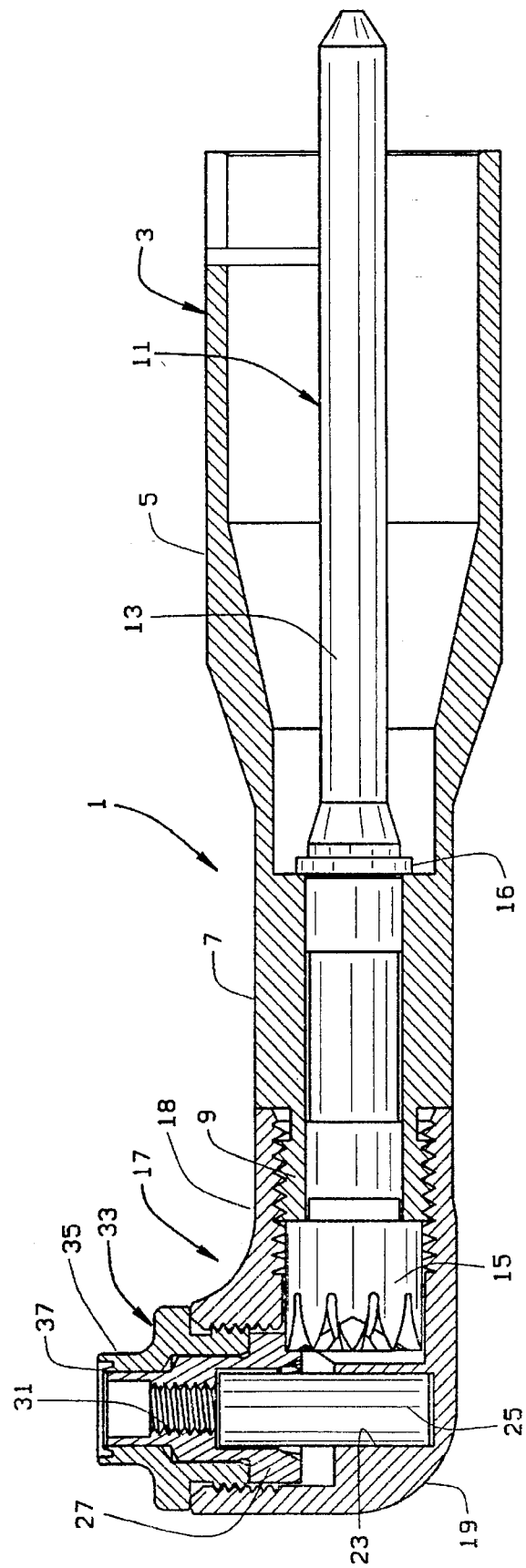
FIG. 1 is a cross-sectional view of a dental prophy angle incorporating one illustrative embodiment of the present invention.
Figure 2:
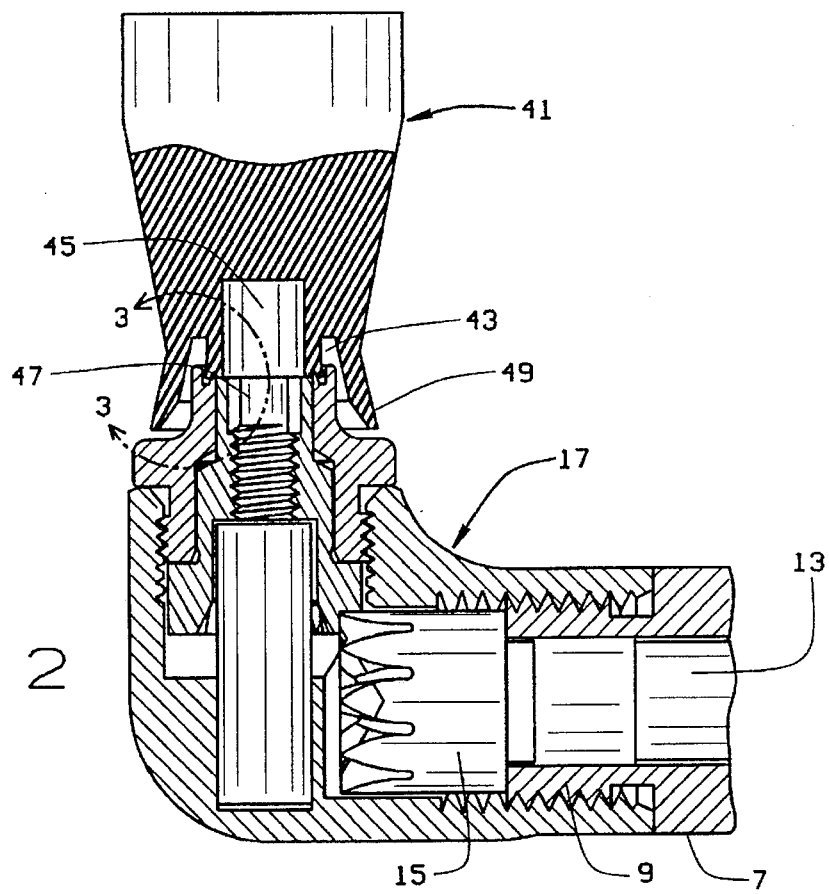
FIG. 2 is a cross-sectional view of the dental prophy angle of FIG. 1, showing a detail of the forward end of the angle with a prophy cup attached.
Figure 3:
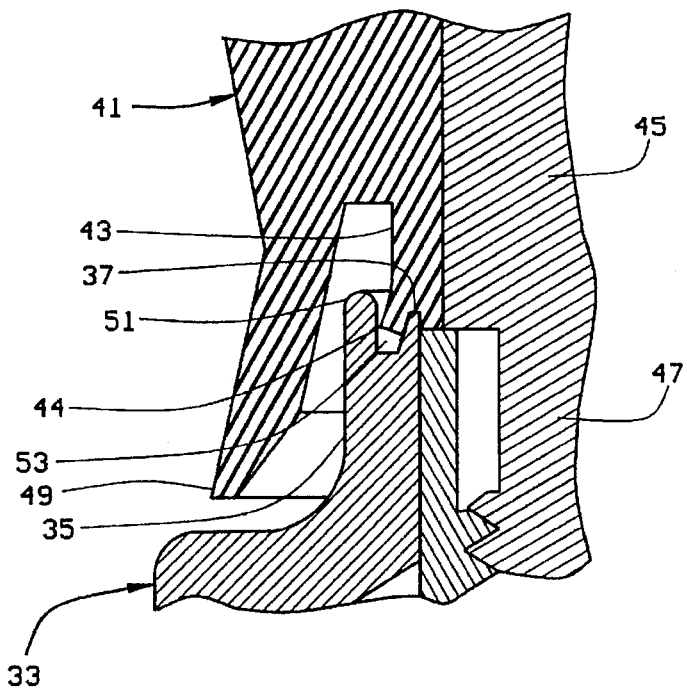
FIG. 3 is an enlarged cross-sectional view taken along line 3—3 of FIG. 2, showing the seal between a cap and prophy cup of FIGS. 1 and 2.
Figure 4:
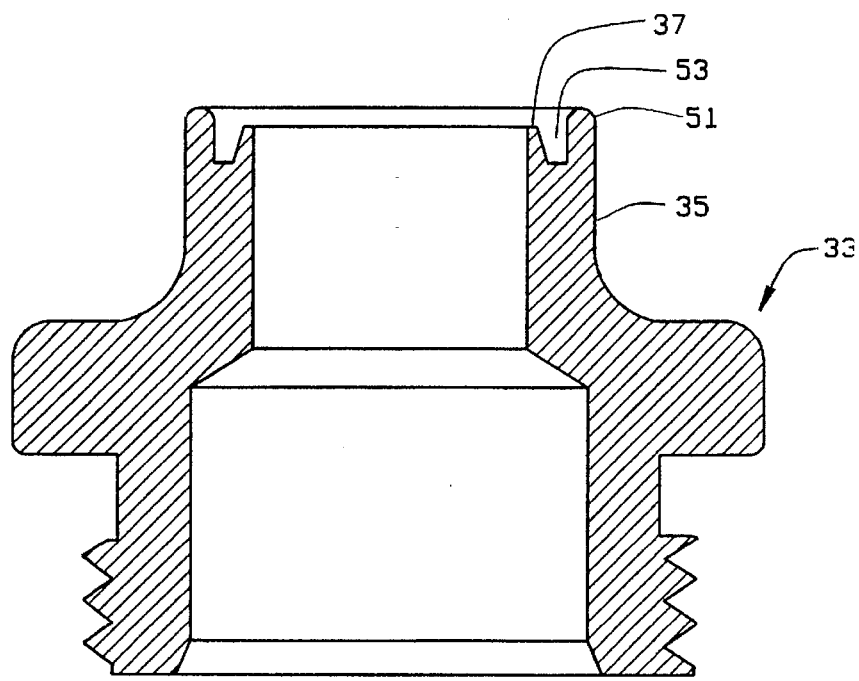
FIG. 4 is a cross-sectional view of a cap of the prophy angle of FIG. 1.
Figure 5:
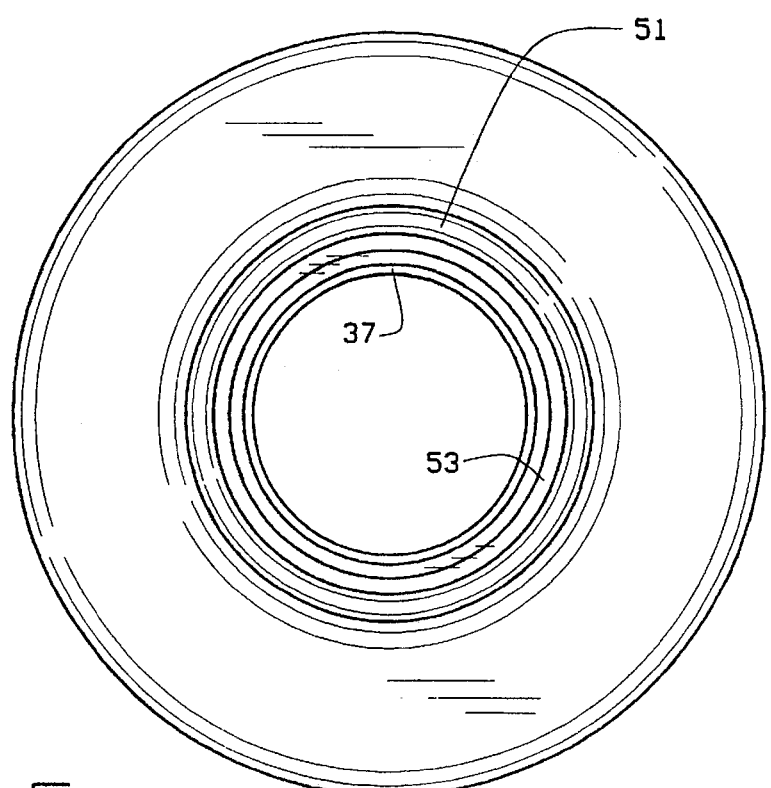
FIG. 5 is a top plan view of the cap of FIG. 4.

Referring now to the drawings, and in particular to FIG. 1, reference numeral 1 indicates a dental prophy angle incorporating a protective wall of the present invention.

The illustrative prophy angle is identical with the angle sold by Young Dental Manufacturing Company of Earth City, Mo. under the trademark TS2, except for the structure of a cap portion. All of the parts are machined from bronze and stainless steel. A first body part 3 includes a sleeve part 5 and neck part 7 which terminates in an externally threaded stud 9. A drive gear member 11 includes a shaft 13 rotatably mounted in an axial bore of the body and a drive gear 15 butted against the forward end of the stud 9. A retaining ring 16 mounted in a groove in the drive shaft 13 limits axial movement of the drive gear member 11.

A second body part 17 is threaded onto the stud 9. The second body part includes a second neck part 18 internally threaded onto the neck part 7 of the first body part 3 and a head part 19. The head part 19 includes an axial bore and a bore extension 23. A post 25 is press fitted into the bore extension 23. The post 25 acts as a thrust bearing for a driven gear 27. The driven gear 27 includes a gear part and an upwardly-extending internally threaded bur tube 31.

A cap 33 is threaded into the open end of the head bore and forms radial bearings for the driven gear. A stem 35 on the upper face of the cap terminates in an externally bevelled knife edge 37, a short distance above the top of the bur tube 31.

Specially designed dental tools, when they are screwed into the bur tube 31, form a seal with the knife edge 37 on the stem 35 and prevent intrusion of material from the patient's mouth into the angle. As described in my U.S. Pat. No. 5,484,284, the dental tool may be a prophy cup 41 which includes a sealing ring 43 coplanar with the bottom of the head 45 of a screw 47 embedded in the cup. When the cup screw 47 is threaded into the bur tube 31, the sealing ring 43 is cut into by the knife edge 37 of the stem 35 and the outer portion of the ring 43 forms a lip 44 which is deflected outwardly by the stem. The cup 41 further includes a peripheral skirt or slinger 49 which extends downwardly and away from the screw 47. The inner surface of the slinger 49 is spaced from the ring 43.

As thus far described, the prophy angle and cup are prior art devices sold by Young Dental Manufacturing Company, under the trademark TS2.

In accordance with the present invention, the cap 33 is formed with an annular protective wall 51 surrounding the hollow stem 35. The wall 51 extends slightly above the stem 35 and is spaced from the stem 35 to form an interstice 53 between the stem 35 and the wall 51. The wall 51 of the preferred embodiment is continuous and is spaced from the stem 35 a sufficient distance to allow the lip 44, formed when the stem cuts into the cup's ring 43, to rotate freely without engaging the wall 51. The bottom of interstice 53 is likewise spaced from the lower edge of lip 44.

The wall 51 protects the knife edge 37 from damage, as might occur, for example, if the angle 1 is dropped or if several of the angles are placed together for cleaning or sterilization.

By way of illustration, for use with a dental tool having a sealing ring 43 with an outer diamer of 0.120", the stem 35 may have an inner diameter of 0.1045" and its knife edge may have an outer diameter of 0.109", the bottom of the interstice 53 may have an inner diameter (root of the stem 35) of 0.118" and an outer diameter (root of the wall 51) of 0.132", and the wall 51 may have an outer diameter of 0.153". The knife edge thus has a nominal thickness of 0.00225" and the wall 51 has a nominal thickness of 0.0105". The wall 51 illustratively has a height of 0.017" above the floor of the interstice 53, and a height of 0.005" above the top of the stem 35.

It has been found that a device made in accordance with the present invention can withstand simulated hard use conditions far better than similar devices without the protective wall 51. A hardened stainless steel cap 33 without the wall 51 was subject to nicking and chipping of the knife edge, while a softer stainless steel cap was subject to denting of the knife edge. The cap 33 of the present invention protected the knife edge without any visible damage or interference with the seal formed with the cups 41.

The foregoing description is set forth only for illustrative purposes and is not meant to be limiting. Numerous variations within the scope of the appended claims will be apparent to those skilled in the art. For example, the wall may be formed around different stems surrounding a bur tube, such as the stem on the cap described in my co-pending U.S. application Ser. No. 08/515,825 entitled "Permanently Lubricated Dental Prophylaxis Angle", and filed on the same date as the present application. Although the dental tool 41 was described to be a prophy cup, other tools, such as brushes, could be used, as long as they have a robber base into which the knife edge can cut to form the seal with the cap. The wall may be crenelated or otherwise interrupted, for example to provide drainage for the interstice 53, although the preferred embodiment has been found not to retain moisture or debris. The wall 51 may be spaced slightly closer to the stem 35; the outside of the lip 44 will then kiss the wall 51, forming a secondary seal, but creating greater friction. These examples are merely illustrative.

I claim:

1. A dental prophylaxis angle comprising a body having a hollow stem thereon, a rotatable bur tube extending into the hollow stem, the hollow stem having a knife edge which extends axially above an axial end of the bur tube, and a protector wall which surrounds the knife edge.

2. The angle of claim 1 wherein the protector wall is taller than the hollow stem.

3. The angle of claim 2 wherein the protector wall is several times the thickness of the knife edge of the stem.

4. The angle of claim 3 wherein the axial opening is threaded to receive a threaded shaft.

5. The angle of claim 2 wherein the knife edge has a thickness of from 0.001" to 0.004".

6. The angle of claim 5 wherein the protector wall has a thickness of at least about 0.008".

7. The angle of claim 2 wherein the protector wall has a thickness of at least about 0.008".

8. The angle of claim 7 wherein the protector wall is spaced about 0.008" to about 0.020" from the knife edge.

9. The angle of claim 2 wherein the protector wall is continuous and of uniform height 0.002" to 0.010" above the knife edge.

10. The angle of claim 1 wherein the bur tube includes an axial opening sized to receive a shaft of a dental tool.

11. In a dental prophylaxis angle comprising a body having a sleeve part housing a rotatable drive gear, a head part housing a rotatable driven gear operatively connected to the drive gear, the driven gear including a bur tube extending upwardly into an opening in the head part, and a continuous upwardly-extending external annular stem surrounding the opening in the head part, the annular stem having a free upper edge for forming a seal with a dental tool attached to the bur tube, the improvement wherein the body includes an upwardly-extending protective shield surrounding the annular stem, the shield having a height greater than the height of the annular stem.

12. The improvement of claim 11 wherein the annular stem has a sharp upper edge for cutting into an elastomeric tool mounted to the bur tube for rotation with the bur tube.

13. The improvement of claim 12 wherein the bur tube is internally threaded for receiving a threaded shaft on the tool.

14. The improvement of claim 11 wherein the shield is a continuous wall.

15. In combination, a dental handpiece including a housing, an annular stem on the housing, the stem having an annular sharp free edge, a rotatable member rotatably received in the housing, the rotatable member having a boss extending into the stem, and a wall surrounding the annular stem to protect the sharp free edge of the stem; and a dental tool including a shaft which is received in the boss to secure the tool to the handpiece and an elastomeric annular ring concentric with the tool shaft, the annular edge of the stem cutting into the elastomeric ring to form a seal, an outer part of the elastomeric ring extending between the stem and the wall.

16. The combination of claim 15 wherein the ring has a diameter less than 1.2 times the diameter of the annular edge of the stem.

17. The combination of claim 15 wherein the wall is continuous.

18. The combination of claim 15 wherein the wall has a height greater than the height of the stem.

19. The combination of claim 15 wherein the tool is a prophylaxis cup.

20. The combination of claim 15 wherein the handpiece includes a prophylaxis angle, the prophylaxis angle having a body rotatably supporting a drive gear and a head rotatably housing a driven gear, the boss being formed on the driven gear and the stem being formed on the head.

21. The combination of claim 20 wherein the head includes a cap, the stem and wall being formed on the cap.

22. The combination of claim 15 wherein the tool includes a skirt spaced radially outward from the ring, the wall extending upwardly between the ring and the skirt.

* * * * *